(12) United States Patent
Mori et al.

(10) Patent No.: US 7,141,263 B2
(45) Date of Patent: Nov. 28, 2006

(54) PROCESS FOR PRODUCING CINNAMALDEHYDE DERIVATIVES, USE THEREOF AND THE LIKE

(75) Inventors: Kenichi Mori, Kawasaki (JP); Shinji Fujita, Kawasaki (JP); Nao Funakoshi, Kawasaki (JP); Tadashi Takemoto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 13 days.

(21) Appl. No.: 11/154,658

(22) Filed: Jun. 17, 2005

(65) Prior Publication Data

US 2005/0245759 A1   Nov. 3, 2005

Related U.S. Application Data

(63) Continuation of application No. 10/295,997, filed on Nov. 18, 2002, now Pat. No. 6,965,055, which is a continuation of application No. PCT/JP01/03545, filed on Apr. 24, 2001.

(30) Foreign Application Priority Data

May 16, 2000   (JP)   ............................. 2000-142811

(51) Int. Cl.
  *A23L 1/236*   (2006.01)
  *C07C 229/00*   (2006.01)
(52) U.S. Cl. ........................................ 426/548; 560/40
(58) Field of Classification Search .................... None
  See application file for complete search history.

(56) References Cited

U.S. PATENT DOCUMENTS

| 2,529,186 | A |   | 11/1950 | Richmond |
|---|---|---|---|---|
| 5,480,668 | A | * | 1/1996 | Nofre et al. ................. 426/548 |
| 5,811,588 | A |   | 9/1998 | Castelijns et al. |
| 6,693,214 | B1 |   | 2/2004 | Kawahara et al. |
| 2003/0118710 | A1 |   | 6/2003 | Kawahara et al. |
| 2005/0014972 | A1 |   | 1/2005 | Kawahara et al. |

FOREIGN PATENT DOCUMENTS

| EP |   1 283 213 A1 | 2/2003 |
|---|---|---|
| WO | WO 99/52937 | 10/1999 |
| WO | WO 01/25260 | 4/2001 |

OTHER PUBLICATIONS

A. Kurtosikova et al., Synthesis of Lignin Model Compounds of the Cinnameldehyde Stilbene and Arylgylcerol Types, Cellulose Chem. Technol., 9, 51-59 (1975).
Organic Reactions, The Aldol Condensation, 1968, pp. 68-79, v.
J.M. Bruce, et al., *J. Chem. Soc. C.*, No. 5, pp. 649-653 (1970).
E. Duran, et al., *Holzforschung*, vol. 46, pp. 21-24 (1992).
Barakat, H.H., et al., *Phytochemistry*, vol. 26, No. 6, pp. 1837-1838 (1987).
US 6,933,408, 08/2005, Kawahara et al. (withdrawn)

* cited by examiner

*Primary Examiner*—Paul A. Zucker
(74) *Attorney, Agent, or Firm*—Oblon, Spivak, McClelland, Maier & Neustadt, P.C.

(57) ABSTRACT

A process for conveniently and efficiently producing a highly pure cinnamaldehyde derivative, for example, (2E)-(3-hydroxy-4-methoxy)cinnamaldehyde, which comprises reacting a benzaldehyde derivative, such as isovanillin and the like, with acetaldehyde in the presence of an alkali, in particular preferably, dropping acetaldehyde little by little thereto in an aqueous solution at a low temperature for the reaction thereof. The cinnamaldehyde derivative thus obtained is selectively reduced to produce 3-(3-hydroxy-4-substituted (with methoxy group or the like)phenyl)propionaldehyde. Further, through a reductive alkylation reaction of the compound thus produced with an aspartame, N-[N-[3-(3-hydroxy-4-substituted (with methoxy group or the like)phenyl)propyl]-L-aspartyl]-L-phenylalanine 1-methyl ester, which is useful as a sweetener having a high sweetening potency, can be industrially and efficiently produced. The processes therefor are also provided.

28 Claims, 2 Drawing Sheets

PROCESS FOR PRODUCING CINNAMALDEHYDE DERIVATIVES, USE THEREOF AND THE LIKE

CONTINUING APPLICATION DATA

This application is a Continuation of U.S. application Ser. No. 10/295,997, filed Nov. 18, 2002, now U.S. Pat. No. 6,965,055, which is a Continuation of International Application Ser. No. PCT/JP01/03545, filed on Apr. 24, 2001, the contents of which is incorporated herein by reference.

BACKGROUND OF THE INVENTION

1. Field of the Invention

The present invention relates to a novel process for producing cinnamaldehyde derivatives, which are useful as various intermediates for production of foods, medicaments and the like, in particular, as an intermediate for production of aspartyl dipeptide ester derivatives, which are superior as a sweetener (sweetening agent) having a high sweetening potency (degree of sweetness), and a use thereof as the intermediates and the like.

2. Discussion of the Background

In recent years, as eating habits have been improved to a high level, weight gain caused by excessive sugar intake and diseases accompanied by weight gain have been at issue. Accordingly, the development of a low-calorie sweetener (sweetening agent), which replaces sugar, has been in strong demand. An example of a sweetener that is widely used at present is Aspartame, which is excellent in terms of safety and quality of sweetness. However, Aspartame is somewhat problematic in terms of stability.

An aspartyl dipeptide ester derivative represented by the following general formula (IV) has been found to be a sweetener, and has excellent stability and is better by far in terms of sweetening potency, i.e., has an advantage in cost per sweet taste (see the Description in the International Patent Publication WO99/52937).

(IV)

In the above formula (IV), R denotes any one of a hydrogen atom, a lower alkyl group having 1 to 4 carbon atoms and a lower alkoxy group having 1 to 4 carbon atoms.

Accordingly, it is an important goal to develop an industrially efficient process for producing such an aspartyl dipeptide ester derivative.

A process for producing the aspartyl dipeptide ester derivative described above efficiently, in particular a production route therefor, and a process for production of the intermediate therefore, have been studied. As a result, it has been found that by reducing a carbon-carbon double bond in a cinnamaldehyde derivative represented by the following general formula (II) selectively, the derivative can be converted into a novel propionaldehyde derivative represented by the following general formula (III) (see the Description in the Japanese Patent Application 11-371284; PCT/JP00/06626), and, on the other hand, that by reacting this aldehyde derivative (III) and an aspartame with hydrogen in the presence of a reduction catalyst for a reductive alkylation reaction, the aspartyl dipeptide ester derivative (IV) which is useful as a sweetener, described above can be industrially and conventionally produced (see the Description in the Japanese Patent Application 11-287398; PCT/JP00/06626).

In the above formulae (II) and (III), R denotes any one of a hydrogen atom, a lower alkyl group having 1 to 4 carbon atoms and a lower alkoxy group having 1 to 4 carbon atoms.

Therefore, it is a purpose of the present invention to produce the cinnamaldehyde derivative represented by the general formula (II) described above industrially and efficiently, and further, by using the compound thus produced, to produce the aspartyl dipeptide ester derivative described above as an objective and an important intermediate thereof (propionaldehyde derivative).

The present inventors have researched and studied on an industrial process for producing the cinnamaldehyde derivative described above. As a result, during the production of such cinnamaldehyde derivative, as shown in the following Reaction Process 1 (see Holzforschung Vol. 46, No. 1, p. 21–24 1992), it has become clear that a process of synthesizing the derivative through 3 steps of reactions starting from cinnamic acid is known. However, it is necessary to use phosgene as a raw material in this process, and thereby this process becomes troublesome, and an yield thereof is also extremely low. Therefore, it is difficult to say that this process is an industrially profitable process to produce the synthetic intermediate described above.

Further, the following Reaction Process 2 (see Cellulose Chem. Technol., 9, 51–59 1975) is also known. In this process, benzaldehydes are used as a starting material, similar to the present invention, but because many reactions are necessary, this process is troublesome, and therefore it is difficult to say that this process is an industrially profitable process.

On the other hand, an aldol reaction is known as a reaction which can be used for a general process of production thereof. For example, in the condition for the aldol reaction described in Organic Reaction, Volume 16 (John Wiley & Sons, Inc. 1968), it is explained that the best result is obtained in the reaction at a temperature of 5 to 25° C. and for a time of 12 to 24 hours. Further, it is thought that the reactivity thereof is affected by a variety of substituent group(s), a position of substitution thereof on a benzene ring and the like, and a prior knowledge showing a fact that an aldol reaction of benzaldehyde derivative having an electron-donating group, such as a hydroxyl group, a methoxy group or the like, with acetaldehyde has been conducted at a high yield, is not found.

In view of the above, the problem to be solved by the present invention is to provide a process for producing the cinnamaldehyde derivative described above industrially and conventionally, and further in a high purity and at a high yield.

SUMMARY OF THE INVENTION

For resolving the above problem, the present inventors have studied earnestly. As a result, as an example, according to the following Reaction Process 3, by reacting a benzaldehyde derivative, which is represented by the following general formula (I), and has particular substituent group(s) in the particular position on the benzene ring thereof, with acetaldehyde under an alkali condition, they have been able to produce the cinnamaldehyde derivative industrially and conventionally, and further, by reacting them under particular condition, they have succeeded in synthesizing a cinnamaldehyde derivative represented by the following general formula (II) as an objective at a high yield, and found that the process for production thereof is extremely superior as an intermediate process for producing the sweetener having a high sweetening potency described above. On the other hand, it has been also found that from an another benzaldehyde derivative wherein a substituent group or a substitution position thereof on the benzene ring changes from that of the benzaldehyde derivative described above, the corresponding cinnamaldehyde derivative is hardly produced in the reaction similar to the above. Further, the cinnamaldehyde derivative obtained in the present invention is a high purity product, and for example, (2E)-(3-hydroxy-4-methoxy)cinnamaldehyde has a melting point of 149 to 152° C., and the melting point thereof is very different from that (123 to 125° C.) of a compound described in the well-known literature described above corresponding to such above compound in the present invention, (I)

Reaction Process 3

(II)

and therefore it is presumed that a purity or a crystal type of the product in the present invention is different from that in the literature.

In the above formulae (I) and (II), R denotes any one of a hydrogen atom, a lower alkyl group having 1 to 4 carbon atoms and a lower alkoxy group having 1 to 4 carbon atoms.

Further, according to the process in the present invention, by adding acetaldehyde to a benzaldehyde derivative represented by the general formula (I) in the presence of an alkali, preferably at a low temperature of 0 to −20° C. and over a period of (during) 12 to 96 hours, preferably, over a period of 24 to 72 hours, a cinnamaldehyde derivative as an objective represented by the following general formula (II) can be synthesized at an extremely high yield (not less than 50%), and a secondary reaction can be minimally suppressed. Accordingly, it has been found that, as compared with the troublesome route described in the literature described above, the process for production thereof in the present invention is industrially superior in a production of a production intermediate, and also the cinnamaldehyde derivative obtained in the present invention is industrially superior as an intermediate for production of the aspartyl dipeptide ester derivative.

On the basis of these various findings, the present invention has been completed.

Thus, the present invention provides a process for producing a cinnamaldehyde derivative represented by the following general formula (II) or a salt thereof:

(II)

comprising:
reacting a benzaldehyde derivative represented by the following general formula (I):

(I)

with acetaldehyde in the presence of an alkali,
wherein R is a hydrogen atom, a lower alkyl group having 1 to 4 carbon atoms, or a lower alkoxy group having 1 to 4 carbon atoms.

The present invention also provides a process for producing a propionaldehyde derivative represented by the following general formula (III):

(III)

comprising:
producing a cinnamaldehyde derivative represented by formula (II) as described above, and
subjecting the cinnamaldehyde derivative representative formula (II) to a reaction for reducing a carbon-carbon double bond selectively with hydrogen in the presence of a reduction catalyst,
wherein R is a hydrogen atom, a lower alkyl group having 1 to 4 carbon atoms, or a lower alkoxy group having 1 to 4 carbon atoms.

In addition, the present invention provides a process for producing an aspartyl dipeptide ester derivative represented by the following general formula (IV) or a salt thereof:

(IV)

comprising:

producing a propionaldehyde derivative represented by formula (III) as described above, and subjecting the propionaldehyde derivative represented by formula (III) and an aspartame to a reductive alkylation reaction, wherein R is a hydrogen atom, a lower alkyl group having 1 to 4 carbon atoms, or a lower alkoxy group having 1 to 4 carbon atoms.

The present invention also provides a process for producing an aspartyl dipeptide ester derivative represented by the following general formula (IV) or a salt thereof:

(IV)

comprising:

producing a cinnamaldehyde derivative represented by formula (II) as described above, and subjecting the cinnamaldehyde derivative represented by formula (II) and an aspartame to a reductive alkylation reaction, wherein R is a hydrogen atom, a lower alkyl group having 1 to 4 carbon atoms, or a lower alkoxy group having 1 to 4 carbon atoms.

Further, the present invention also provides a crystal of (2E)-(3-hydroxy-4-methoxy)cinnamaldehyde having a purity of at least 95% by weight and a melting point of at least 145° C.

A more complete appreciation of the invention and many of the attendant advantages thereof will be readily obtained as the same becomes better understood by reference to the following Figures in conjunction with the detailed description below.

DETAILED DESCRIPTION OF THE INVENTION

In the present invention, the cinnamaldehyde derivative (II), for example (2E)-(3-hydroxy-4-methoxy)cinnamaldehyde, can be industrially and conventionally produced from the benzaldehyde derivative (I), for example isovanillin, and further, it can be produced at a high yield and at a high purity. The cinnamaldehyde derivative thus obtained is used, and a reaction for reducing a carbon-carbon double bond in the derivative selectively can be conducted to produce 3-(3-hydroxy-4-substituted (with methoxy group or the like) phenyl)propionaldehyde. Further, through a reductive alkylation reaction of the compound thus produced with an aspartame, an aspartyl dipeptide ester derivative, which is useful as a sweetener having a high sweetening potency, for example N-[N-[3-(3-hydroxy-4-methoxyphenyl)propyl]-L-α-aspartyl]-L-phenylalanine 1-methyl ester can be industrially and efficiently produced.

As a result, the cinnamaldehyde derivative described above, which is obtained in the present invention is extremely useful as an intermediate for production of the aspartyl dipeptide ester derivative, which is useful as a sweetener having a high sweetening potency, described above, or is extremely useful also in production of an important intermediate for the aspartyl dipeptide ester derivative described above, for example 3-(3-hydroxy-4-substituted (with methoxy group or the like)phenyl)propionaldehyde.

Further, (2E)-(3-hydroxy-4-methoxy)cinnamaldehyde in the high purity crystalline form, particularly expected as an intermediate for production thereof described above is also provided.

Hereinafter, the embodiments for carrying out the present invention are explained.

As regards a process for producing the two kinds of aldehyde derivative represented by the general formulae (II) and (III) described above with a use of isovanillin as a starting material according to the Reaction Process 3 described above, by showing a preferable example, and based on this example, it is explained in detail. However, this is a preferable example, and, therefore, as far as the content does not vary from the subject matter of the present invention described herein, the present invention is not limited to this example.

In case of producing the compound (II) described above, an aldol reaction in the first stage is conducted in the presence of an alkali. It can be conducted by using a solvent, and as for the solvent used in this case, there is no particular limitations thereto, as far as a material inactive to a ground substance for reaction, a catalyst and a product may be used therefor. Preferably, water, alcohols, such as methanol and the like, a mixed solvent of alcohol(s) with water, and the like are used, and water is most preferably used.

As for the alkali used in the present invention, there are no particular limitations thereto. An inorganic alkali substance and an organic alkali substance can be used therefor.

For example, a metal hydroxide, such as sodium hydroxide, potassium hydroxide and the like, and amines, such as diethylamine and the like can be conventionally used therefor.

As for an amount used of the alkali employed in the present invention, there is no particular limitations thereto. In case that much excess of the alkali is employed to the benzaldehyde derivative, for example isovanillin, the reaction can be conducted in a shorter time to completion. From the economical point of view, preferably not more than 20 molar equivalents, and more preferably 5 to 15 molar equivalents or so, of the alkali to the benzaldehyde derivative, for example, isovanillin, may be employed.

As for an amount used of the acetaldehyde to the benzaldehyde derivative, for example isovanillin, there is no particular limitations thereto, and preferably not less than 1 molar equivalent, and more preferably 1.5 to 3 molar equivalents or so of the acetaldehyde thereto can be employed therefor.

As for a reaction temperature, in particular, the reaction is preferably conducted at a low temperature. Preferably at −20 to 5° C. or so, more preferably at −20 to 3° C. or so, further preferably at −20 to 0° C. or so and in particular preferably at −15 to −5° C. or so, the reaction i conducted, and also, the reaction is preferably conducted in water to promote the reaction. Outside this temperature range, the higher the reaction temperature is, the more the secondary reaction proceeds, and on the other hand, the lower the reaction temperature is, the reaction speed becomes extremely slow, and therefore these cases are not preferable.

In the present invention, the reaction is conducted at the low temperature as described above, and additionally, acetaldehyde is dropped preferably over (during) a long period of time. As for the time for dropping the acetaldehyde, preferably not less than 12 hours, more preferably 12 to 96 hours or so, and further preferably 24 to 72 hours or so may be selected. Outside this range of time, the shorter the reaction time is, the more the secondary reaction proceeds, and even if the reaction is conducted for a further long time, the yield does not improve, and therefore, these cases are not preferable.

In the cinnamaldehyde derivative produced in the present invention, any one of the free form and the salt form thereof are contained, and according to the following reaction or the like, the form thereof can be selected.

(3-Hydroxy-4-methoxy)cinnamaldehyde produced in the above described manner has a particularly high purity, and is preferably used as an intermediate. As understood also from the physical properties in the following Examples, the purity thereof is extremely high. It has a purity of, preferably not less than 95% by weight, and more preferably not less than 97% by weight. A melting point thereof is preferably at least 140° C., and more preferably not less than 145° C., and therefore it is clear that the melting point thereof is very different from that of the compound corresponding thereto, which is shown in the prior literature described above. Accordingly, it is thought that the purity or a crystal type of the compound in the present invention is different from that described in the literature.

In case of producing the propionaldehyde derivative (III) as an objective from the cinnamaldehyde derivative (II) having a carbon-carbon double bond, which is obtained in the above reaction, for example in case of producing 3-(3-hydroxy-4-methoxyphenyl)propionaldehyde from the (2E)-(3-hydroxy-4-methoxy)cinnamaldehyde, the cinnamaldehyde derivative (II) described above may be subjected to a reaction for reducing only carbon-carbon double bond in the derivative selectively by reacting hydrogen therewith in the presence of a catalyst.

In the above formula (III), R denotes any one of a hydrogen atom, a lower alkyl group having 1 to 4 carbon atoms and a lower alkoxy group having 1 to 4 carbon atoms.

As for this reduction reaction, the reaction can be conducted in the presence of a solvent. As for the solvent employed in this case, there is no particular limitations thereto, as far as a material inactive to a ground substance for reaction, a catalyst and a product may be employed therefor, and a homogeneous organic solvent (a singular solvent consisting of one kind of solvent or a mixed solvent consisting of plural solvents) or a mixed solvent of such organic solvent(s) with water can be cited therefor. For the organic solvent(s), for example, methanol, ethanol, tetrahydrofuran, acetonitrile, dimethylformamide and the like can be cited. Preferably, a lower alcohol, such as methanol and the like, can be cited therefor. In particular, methanol is preferably used.

For the catalyst, a catalyst for hydrogenation may be used, and a reduction catalyst, which is typically used as a general catalyst for hydrogenation, such as, preferably palladium-, platinum- and rhodium-based catalysts, and the like can be cited as a preferable example.

For a hydrogen pressure, preferably 0.01 to 1.0 MPa or so, and more preferably 0.01 to 0.1 MPa or so can be selected.

As regards a temperature for conducting the reaction and the reaction time, a condition suitable for a hydrogenation reaction can be selected. In order to suppress a secondary reaction and to promote much more the desired reaction, a reaction temperature in a range of preferably 25 to 50° C. or so, and more preferably 30 to 40° C. or so, and a reaction time in a range of preferably 2 to 96 hours or so, and more preferably 5 to 48 hours or so, can be suitably selected respectively.

As for a ratio of the cinnamaldehyde derivative used as the starting material for this reaction to the catalyst, though it may be varied with a kind of the catalyst used, for example a range of 0.1 to 30% by weight or so, preferably 0.1 to 2% by weight or so, and more preferably 0.2 to 1% by weight or so of the cinnamaldehyde derivative to the catalyst can be selected for the reaction.

In case that, from the propionaldehyde derivative (III) thus obtained through hydrogenation, for example 3-(3-hydroxy-4-methoxyphenyl)propionaldehyde, N-[N-[3-(3-hydroxy-4-substituted (with methoxy group or the like) phenyl)propyl]-L-aspartyl]-L-phenylalanine 1-methyl ester represented by the following general formula (IV) is produced, there is no particular difficulties therein, and by alkylating reductively this propionaldehyde derivative with -L-aspartyl-L-phenylalanine 1-methyl ester (aspartame) under a condition for hydrogenation, it can be easily produced. Concretely, a suitable solvent is used for the reductive alkylation reaction, and by conducting the reductive alkylation reaction thereof with hydrogen in the solvent, for example acetonitrile, acetic acid, ethyl acetate, alcohol, alcohol containing water and the like, in the presence of a catalyst used for a reductive alkylation reaction, for example a catalyst for hydrogenation, such as palladium-, platinum-, rhodium-based catalyst and the like, and more preferably under a suitable or effective reaction temperature (for example, 15 to 50° C. or so) and pressure (for example, 0.1 to 1.0 MPa or so), the object compound described above can be produced.

(IV)

In the above formula (IV), R denotes any one of a hydrogen atom, a lower alkyl group having 1 to 4 carbon atoms and a lower alkoxy group having 1 to 4 carbon atoms.

Besides, even though in the reductive alkylaion reaction with an aspartame, the cinnamaldehyde derivative (II) described above may be used in place of the propionaldehyde derivative (III) described above as the starting material, similar to the above, the aspartyl dipeptide ester derivative described above can be produced.

In case that, from a reaction mixture obtained by producing the aspartyl dipeptide ester derivative through the reductive alkylation reaction described above, the object compound is separated for purification, there are no particular difficulties therein. After the catalyst used for the reaction is removed therefrom, and if necessary, through a purification method, such as a purification by chromatography, a process for crystallization and the like, a high purity of the aspartyl dipeptide ester derivative which is a sweetener having a high sweetening potency described above as an objective, can be separated therefrom.

The aspartyl dipeptide ester derivative thus obtained can be also obtained in the salt form through a salt-formation process or the like, if necessary.

EXAMPLES

Having generally described this invention, a further understanding can be obtained by reference to certain specific examples which are provided herein for purposes of illustration only and are not intended to be limiting unless otherwise specified.

Example 1

Synthesis of
(2E)-(3-hydroxy-4-methoxy)cinnamaldehyde

Isovanillin (121.72 g, 0.8 mol) and sodium hydroxide (320 g, 8 mol) were dissolved in water (2000 ml) at 30° C., and thereafter the mixture was cooled until to −10° C. A 28 wt % of acetaldehyde aqueous solution (290 g, 1.84 mol) was continuously dropped to this alkali solution for 45 hours. The reaction solution at a time when the drop of the acetaldehyde aqueous solution was finished, was determined by a high performance liquid chromatography (HPLC), and as a result the object compound was produced at an yield of 74%. After the drop was finished, the reaction solution was stirred for 1 hour, and thereafter, by adding a 36 wt % of hydrochloric acid (HCl) aqueous solution (768.1 g, 7.78 mol) thereto, the reaction was stopped. The reaction solution thus obtained was filtered to obtain crystals (324 g). The crystals thus obtained were dispersed in a water (500 ml) at 25° C., and thereafter was dissolved therein by adding a 25 wt % of sodium hydroxide aqueous solution (97.5 g) thereto. Activated carbon (4 g) and celite (16 g) were added to the solution thus obtained, and the mixture was stirred for 1 hour, and thereafter the activated carbon and celite added were filtered for separation. The aqueous solution obtained was neutralized by adding a 36% of hydrochloric acid aqueous solution (55.4 g) thereto. The crystals obtained (185.5 g) were dried under reduced pressure. The dried crystals were dispersed in a methanol (275 ml) at 60° C., and the mixture was stirred for 2 hours. And thereafter the mixture was cooled until to a room temperature, and a slurry thus obtained was filtered. The wet crystals thus obtained (96 g) were dried to obtain (2E)-(3-hydroxy-4-methoxy)cinnamaldehyde (83.2 g, yield: 57%, purity: 98%).

Example 2

Physical properties on
(2E)-(3-hydroxy-4-methoxy)cinnamaldehyde

The physical properties on the title compound obtained in the present invention were in the followings.

Color: Lemon yellow crystal.

Figure 1:
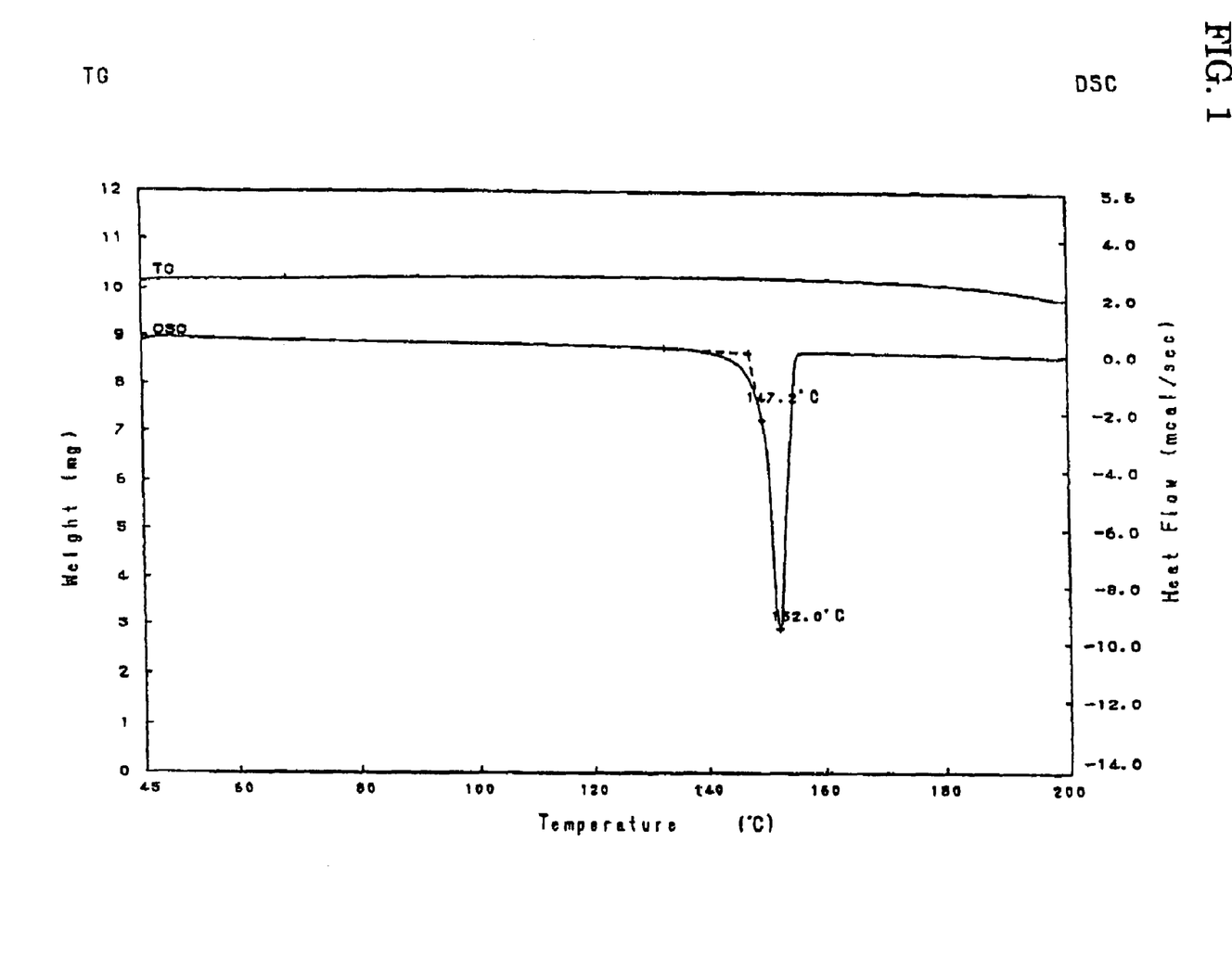
FIG. 1: results of a Differential Scanning Caloriemetry on a crystal of (2E)-(3-hydroxy-4-methoxy)cinnamaldehyde.
TG: Thermogravimetry;
DSC: Differential Scanning Caloriemetry.

(Differential Thermal Analysis)
Temperature range for determination: 50 to 200° C., heating-up speed: 5° C./min., melting point: 147° C. (See FIG. 1.).

(NMR Spectrum)
$^1$H-NMR (DMSO-d6): 3.84 (s, 3H), 6.61 (dd, J=7.8, J=15.8, 1H), 7.01 (d, J=8.25, 1H), 7.15 to 7.20 (m, 2H), 7.60 (d, J=15.8), 9.30 (s, 1H), 9.60 (d, J=7.8, 1H).

$^{13}$C-NMR (DMSO-d6): $C_1$150.912, $C_2$114.817, $C_3$122.056, $C_4$127.150, $C_5$112.207, $C_6$146.959, $C_7$153.898, $C_8$126.339, $C_9$194.189, $C_{10}$55.847.

Figure 2:
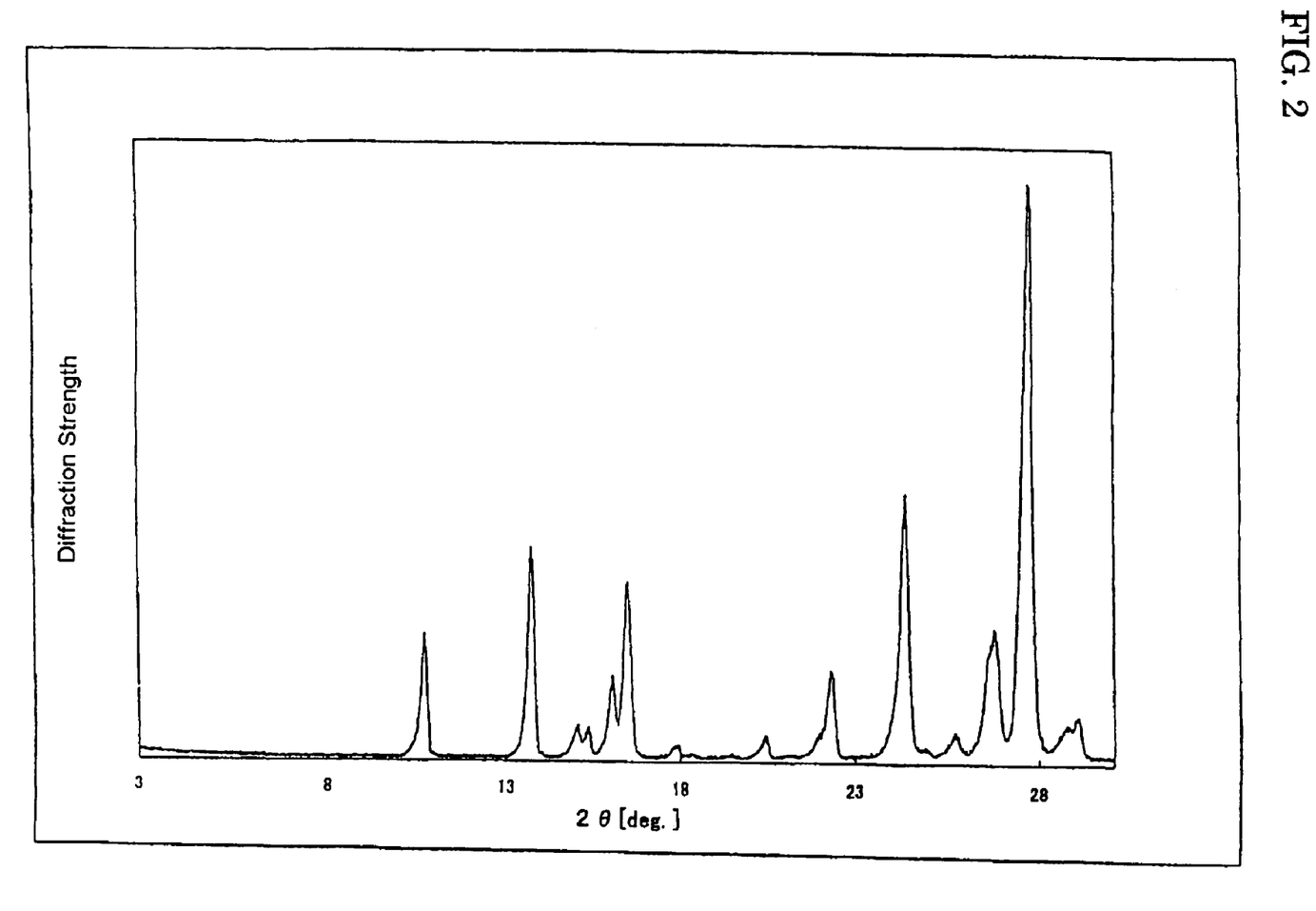
FIG. 2: powder X-ray diffractometry (diffraction method) on a crystal of (2E)-(3-hydroxy-4-methoxy)cinnamaldehyde.

(Powder X-ray Diffraction)
Characteristic peaks of diffractive X-ray were shown in diffraction angles of 13.75°, 16.53°, 24.43° and 27.75° (2, CuK ray) (See FIG. 2.).

From the above, in the present invention, a crystal of (2E)-(3-hydroxy-4-methoxy)cinnamaldehyde having a purity of at least 95% by weight and a melting point of at lowest 145° C. is also contained. In particular, a crystal thereof, which shows peaks of diffractive X-ray in at least diffraction angles of 13.75°, 16.53°, 24.43° and 27.75° (2, CuK ray) when determined in the powder X-ray diffractometry (diffraction method), is preferable.

Example 3

Synthesis of
3-(3-hydroxy-4-methoxyphenyl)propionaldehyde (2E)-(3-hydroxy-4-methoxy)cinnamaldehyde (5.00 g, 0.028 mol) and 5% palladium on alumina (300 mg) were added to methanol (80 ml), and the mixture was stirred for reaction under an atmosphere of mixed gas of nitrogen-hydrogen of ordinary pressure (0.1 MPa) at 35° for 24 hours. The catalyst was removed from the reaction solution by filtering, and further, was washed with methanol (10 ml). The methanol solution obtained was determined quantitatively by a high performance liquid chromatography (HPLC), and as a result 3-(3-hydroxy-4-methoxyphenyl)propionaldehyde (4.38 g, 0.024 mol, yield: 87%) was produced.

Example 4

Synthesis of N-[N-[3-(3-hydroxy-4-methoxyphenyl)propyl]-L-aspartyl]-L-phenylalanine 1-methyl ester A 3-(3-hydroxy-4-methoxyphenyl)propionaldehyde (1.50 g, 0.00832 mol)/methanol solution (8.15 g) and aspartame (2.57 g, 0.00874 mol) were added to a mixed solvent (86 ml) of methanol with water (mixing ratio: 4:1 v/v), and 10% palladium on carbon (containing 50% water) (0.77 g) were added to this mixture. And thereafter, the mixture was stirred for reaction under a hydrogen atmosphere of ordinary pressure (0.1 MPa) at 35° C. for 48 hours. After the reaction was finished, the catalyst was removed therefrom by filtering, and further washed with methanol (20 ml). The filtrate and the wash solution were mixed together, and thereafter the mixture thus obtained was subjected to a quantitative determination by HPLC, and as a result N-[N-[3-(3-hydroxy-4-methoxyphenyl)propyl]-L-aspartyl]-L-phenylalanine 1-methyl ester (2.69 g, 0.00587 mol, yield: 71%) was produced.

Example 5

Synthesis of (2E)-(3-hydroxy-4-methoxy)cinnamaldehyde

A reaction was all conducted in the same reaction condition as that in Example 1 except that the time for dropping the acetaldehyde aqueous solution continuously to the alkali solution was 2 hours without changing any other reaction condition in Example 1. The object compound in the reaction solution was determined quantitatively by a HPLC to give an yield of 38%.

Example 6

Synthesis of (2E)-(3-hydroxy-4-methoxy)cinnamaldehyde

A reaction was conducted in the same reaction condition as that in Example 1, except that the reaction was conducted at a temperature of 5° C. without changing any other reaction condition in Example 1. The object compound in the reaction solution was determined quantitatively by a HPLC to give an yield of 64%. Further, a purity of the crystals obtained was 90%.

Comparative Example 1

Synthesis of (2E)-(3-methoxy-4-hydroxy)cinnamaldehyde

The Example 1 was repeated except that vanillin in the same amount (121.72 g, 0.8 mol) to that of the isovanillin was used in place of the isovanillin without changing any other reaction condition in Example 1. The desired reaction did not proceed to any significant extent. An yield of the title compound produced in the reaction mixture was less than 1% (by weight).

Example 7

Synthesis of (2E)-(3-hydroxy-4-methoxy)cinnamaldehyde-2

Isovanillin (121.72 g, 0.8 mol) and sodium hydroxide (320 g, 8 mol) were dissolved in a water (2000 ml) at 30° C., and thereafter the mixture was cooled until to −10° C. A 28 wt % of acetaldehyde aqueous solution (290 g, 1.84 mol) were continuously dropped to this alkali solution for 45 hours. The reaction solution at a time when the dropping of the acetaldehyde aqueous solution was finished, was determined by a HPLC, and as a result the object compound was produced at an yield of 74%. After the dropping was finished, the reaction solution was stirred for 1 hour, and thereafter, by adding a 36 wt % of hydrochloric acid aqueous solution (768.1 g, 7.78 mol) to this solution, the reaction was stopped. The reaction solution thus obtained was filtered to obtain crystals (324 g). The crystals thus obtained were dispersed in methanol (340 ml), and a slurry thus obtained was filtered. The wet crystals obtained (214 g) were dispersed in methanol (335 ml) at 60° C., and the mixture was stirred for 2 hours. And thereafter the mixture was cooled until to a room temperature, and a slurry thus obtained was filtered. The crystals thus obtained (99 g) were completely dissolved in methanol (1200 ml) at 60° C., and thereafter the mixture was cooled until to 15° C. The crystals obtained were dried to obtain (2E)-(3-hydroxy-4-methoxy)cinnamaldehyde (75 g, yield: 53%, purity: 99.7%).

Example 8

Synthesis of N-[N-[3-(3-hydroxy-4-methoxyphenyl)propyl]-L-aspartyl]-L-phenylalanine 1-methyl ester-2

Aspartame (24.75 g, 0.0841 mol) and 10% platinum on carbon (containing 53% water) (1.98 g) were dispersed in methanol (290 ml) under a hydrogen atmosphere of ordinary pressure (0.1 MPa), and a reaction was conducted by dropping a 3-(3-hydroxy-4-methoxyphenyl)propionaldehyde (14.4 g, 0.08 mol)/methanol solution (112.5 g) to this mixture at 25° C. for 6 hours while stirring. After the reaction was finished, the catalyst was removed by filtering, and further washed with a 50% of methanol aqueous solution (20 ml). The filtrate and the wash solution were mixed together, and thereafter was determined quantitatively by a HPLC to produce N-[N-[3-(3-hydroxy-4-methoxyphenyl)propyl]-L-aspartyl]-L-phenylalanine 1-methyl ester (33.5 g, 0.073 mol, yield: 91%).

Obviously, numerous modifications and variations of the present invention are possible in light of the above teachings. It is therefore to be understood that within the scope of the appended claims, the invention may be practiced otherwise than as specifically described herein.

This application is based on Japanese Patent Application Serial No. JP2000-142811, filed on May 16, 2000, and incorporated herein by reference.

The invention claimed is:

1. A process for producing an aspartyl dipeptide ester derivative represented by the following formula (IV) or a salt thereof:

wherein R is a hydrogen atom, a lower alkyl group having 1 to 4 carbon atoms, or a lower alkoxy group having 1 to 4 carbon atoms,
comprising:
reacting a benzaldehyde derivative represented by the following formula (I):

with acetaldehyde in the presence of an alkali, to produce a a cinnamaldehyde derivative represented by the following formula (II) or a salt thereof:

subjecting the cinnamaldehyde derivative representative formula (II) to a reaction for reducing a carbon-carbon double bond selectively with hydrogen in the presence of a reduction catalyst, to produce a propionaldehyde derivative represented by the following formula (III):

subjecting the propionaldehyde derivative represented by formula (III) and an aspartame to a reductive alkylation reaction, wherein R is a hydrogen atom, a lower alkyl group having 1 to 4 carbon atoms, or a lower alkoxy group having 1 to 4 carbon atoms.

2. The process as defined in claim 1, wherein R is a hydrogen atom.

3. The process as defined in claim 1, wherein R is a lower alkyl group having 1 to 4 carbon atoms.

4. The process as defined in claim 1, wherein R is a lower alkoxy group having 1 to 4 carbon atoms.

5. The process as defined in claim 1, wherein R is a methoxy group.

6. The process as defined in claim 1, wherein the reaction of the benzaldehyde derivative with acetaldehyde is conducted in an aqueous solution at a temperature in the range of 0 to −20° C.

7. The process as defined in claim 1, in which the acetaldehyde is added to the benzaldehyde derivative in an aqueous solution over a period of 12 to 96 hours.

8. The process as defined in claim 7, in which the acetaldehyde is added to the benzaldehyde derivative in an aqueous solution at a temperature in the range of 0 to −20° C. over a period of 12 to 96 hours.

9. The process as defined in claim 1, in which the acetaldehyde is added to the benzaldehyde derivative in an aqueous solution at a temperature in the range of 0 to −20° C. over a period of 12 to 96 hours.

10. The process as defined in claim 1, wherein the cinnamaldehyde derivative is (2E)-(3-hydroxy-4-methoxy)cinnamaldehyde.

11. The process as defined in claim 1, in which the acetaldehyde is added to isovanillin in an aqueous solution at a temperatue in the range of 0 to −20° C. over a period of 12 to 96 hours, and wherein the cinnamaldehyde derivative is in a crystalline form having a melting point of at least 140° C.

12. The process as defined in claim 1, wherein the alkali is a metal hydroxide or an amine.

13. The process as defined in claim 1, wherein the reaction for reducing a carbon-carbon double bond selectively is a hydrogenation reaction in the presence of a catalyst for hydrogenation.

14. The process as defined in claim 1, wherein the reduction catalyst is a palladium-, platinum-, or rhodium-based catalyst.

15. A process for producing an aspartyl dipeptide ester derivative represented by the following formula (IV) or a salt thereof:

wherein R is a hydrogen atom, a lower alkyl group having 1 to 4 carbon atoms, or a lower alkoxy group having 1 to 4 carbon atoms, comprising:

reacting a benzaldehyde derivative represented by the following formula (I):

with acetaldehyde in the presence of an alkali, to produce a a cinnamaldehyde derivative represented by the following formula (II) or a salt thereof:

and subjecting the cinnamaldehyde derivative represented by formula (II) and an aspartame to a reductive alkylation reaction.

16. The process as defined in claim 15, wherein R is a hydrogen atom.

17. The process as defined in claim 15, wherein R is a lower alkyl group having 1 to 4 carbon atoms.

18. The process as defined in claim 15, wherein R is a lower alkoxy group having 1 to 4 carbon atoms.

19. The process as defined in claim 15, wherein R is a methoxy group.

20. The process as defined in claim 15, wherein the reaction of the benzaldehyde derivative with acetaldehyde is conducted in an aqueous solution at a temperature in the range of 0 to −20° C.

21. The process as defined in claim 15, in which the acetaldehyde is added to the benzaldehyde derivative in an aqueous solution over a period of 12 to 96 hours.

22. The process as defined in claim 21, in which the acetaldehyde is added to the benzaldehyde derivative in an aqueous solution at a temperature in the range of 0 to −20° C. over a period of 12 to 96 hours.

23. The process as defined in claim 15, in which the acetaldehyde is added to the benzaldehyde derivative in an aqueous solution at a temperature in the range of 0 to −20° C. over a period of 12 to 96 hours.

24. The process as defined in claim 15, wherein the cinnamaldehyde derivative is (2E)-(3-hydroxy-4-methoxy) cinnamaldehyde.

25. The process as defined in claim 15, in which the acetaldehyde is added to isovanillin in an aqueous solution at a temperatue in the range of 0 to −20° C. over a period of 12 to 96 hours, and wherein the cinnamaldehyde derivative is in a crystalline form having a melting point of at least 140° C.

26. The process as defined in claim 15, wherein the alkali is a metal hydroxide or an amine.

27. A method of producing a sweetened food or medicinal product, comprising producing the aspartyl dipeptide ester derivative according to claim 1, and incorporating the dipeptide ester derivative into a food or medicinal product.

28. A method of producing a sweetened food or medicinal product, comprising producing the aspartyl dipeptide ester derivative according to claim 15, and incorporating the aspartyl dipeptide ester derivative into a food or medicinal product.

* * * * *

UNITED STATES PATENT AND TRADEMARK OFFICE
CERTIFICATE OF CORRECTION

PATENT NO. : 7,141,263 B2 Page 1 of 1
APPLICATION NO. : 11/154658
DATED : November 28, 2006
INVENTOR(S) : Kenichi Mori et al.

It is certified that error appears in the above-identified patent and that said Letters Patent is hereby corrected as shown below:

Column 9, Line 24:
"reaction i conducted" should read --reaction is conducted--.

Column 13, Line 44:
"give an yield" should read --give a yield--;

Line 56:
"give an yield" should read --give a yield--.

Column 14, Line 1:
"An yield" should read --A yield--;

Line 20:
"an yield" should read --a yield--.

Signed and Sealed this

Twenty-ninth Day of May, 2007

JON W. DUDAS
*Director of the United States Patent and Trademark Office*